US011786670B2

(12) United States Patent
Cronenberg

(10) Patent No.: US 11,786,670 B2
(45) Date of Patent: *Oct. 17, 2023

(54) PEN NEEDLE REMOVAL DEVICE FOR A DRUG DELIVERY DEVICE

(71) Applicant: Becton, Dickinson and Company, Franklin Lakes, NJ (US)

(72) Inventor: Richard Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/993,163

(22) Filed: Aug. 13, 2020

(65) Prior Publication Data

US 2020/0368450 A1 Nov. 26, 2020

Related U.S. Application Data

(63) Continuation of application No. 15/863,655, filed on Jan. 5, 2018, now Pat. No. 10,744,273, which is a
(Continued)

(51) Int. Cl.
*A61M 5/32* (2006.01)
*A61M 5/24* (2006.01)
*A61M 5/315* (2006.01)

(52) U.S. Cl.
CPC ........ *A61M 5/3213* (2013.01); *A61M 5/3202* (2013.01); *A61M 5/3276* (2013.01);
(Continued)

(58) Field of Classification Search
CPC .............. A61M 5/3213; A61M 5/3202; A61M 5/3276; A61M 5/24; A61M 5/31525;
(Continued)

(56) References Cited

U.S. PATENT DOCUMENTS 5,312,346 A 5/1994 Han
5,829,589 A 11/1998 Nguyen
(Continued)

FOREIGN PATENT DOCUMENTS

DE 102005054075 5/2007
DE 102005061637 A1 7/2007
(Continued)

*Primary Examiner* — Amber R Stiles
(74) *Attorney, Agent, or Firm* — Dickinson Wright PLLC

(57) ABSTRACT

A removal device (121, 221) for removing and disposing of a pen needle (113, 213) connectable to a drug delivery device (111, 211) includes a body (123, 223) having a cavity (141, 241) for receiving the pen needle of the drug delivery device such that a patient end (116, 216) of a needle (115, 215) of the pen needle is covered by the body. An ejector (151, 251) is movably connected to the body (123, 223) for engaging the received pen needle (113, 213) and selectively ejecting the engaged pen needle from the body. The pen needle (113, 213) is securely retained within the removal device (121, 221) without exposing the needle (115, 215) of the pen needle until the pen needle (113, 213) can be properly disposed of, such as in a sharps container, thereby substantially preventing an accidental needle stick.

19 Claims, 11 Drawing Sheets

Related U.S. Application Data continuation of application No. 14/517,395, filed on Oct. 17, 2014, now Pat. No. 9,861,760, which is a continuation of application No. 13/513,159, filed as application No. PCT/US2010/003086 on Dec. 3, 2010, now Pat. No. 8,882,706.

(60) Provisional application No. 61/266,623, filed on Dec. 4, 2009.

(52) U.S. Cl.
CPC ........... *A61M 5/24* (2013.01); *A61M 5/31525* (2013.01); *A61M 5/31533* (2013.01); *A61M 2005/2407* (2013.01); *A61M 2005/3206* (2013.01); *A61M 2005/3208* (2013.01); *A61M 2207/10* (2013.01); *Y10T 29/49822* (2015.01); *Y10T 29/53* (2015.01)

(58) Field of Classification Search
CPC ...... A61M 5/31533; A61M 2005/2407; A61M 2005/3206; A61M 2005/3208; A61M 2207/10; Y10T 29/49822; Y10T 29/53
See application file for complete search history.

(56) References Cited

U.S. PATENT DOCUMENTS

| | | | |
|---|---|---|---|
| 5,968,021 | A | 10/1999 | Ejlersen |
| 6,880,701 | B2 | 4/2005 | Bergeron |
| 6,889,830 | B2 | 4/2005 | Bergeron |
| 6,923,319 | B1 | 8/2005 | Erickson |
| 7,207,976 | B2 | 4/2007 | Hansen |
| 7,214,212 | B2 | 5/2007 | Pommereau |
| 7,654,981 | B2 | 2/2010 | Lehmann |
| 8,057,444 | B2 | 11/2011 | Hartmann |
| 8,882,706 | B2 | 11/2014 | Cronenberg |
| 9,861,760 | B2 * | 1/2018 | Cronenberg ........ A61M 5/3213 |
| 10,744,273 | B2 * | 8/2020 | Cronenberg ........ A61M 5/3213 |
| 2002/0068908 | A1 | 6/2002 | Sun |
| 2005/0016883 | A1 | 1/2005 | Phan |
| 2005/0269226 | A1 | 12/2005 | Erickson |
| 2007/0299394 | A1 | 12/2007 | Rolfe |
| 2009/0014462 | A1* | 1/2009 | Costa ................ A61M 5/3205 221/185 |
| 2010/0262088 | A1 | 10/2010 | Hartmann |
| 2011/0077615 | A1 | 3/2011 | Schraga |
| 2011/0092952 | A1 | 4/2011 | Voellmicke |
| 2011/0178471 | A1 | 7/2011 | Voellmicke |
| 2012/0029440 | A1 | 2/2012 | Boyd |

FOREIGN PATENT DOCUMENTS

| | | |
|---|---|---|
| DE | 102007022404 | 11/2008 |
| EP | 01830907 | 4/2009 |
| EP | 2381985 | 7/2010 |
| EP | 02298390 | 3/2011 |
| EP | 2316510 | 5/2011 |
| EP | 2316513 | 5/2011 |
| WO | 05068153 | 7/2005 |
| WO | 2005079889 A1 | 9/2005 |
| WO | 2006009508 A1 | 1/2006 |
| WO | 06064231 | 6/2006 |
| WO | 2008067467 | 6/2008 |
| WO | 2008138319 | 11/2008 |
| WO | 10084306 | 7/2010 |
| WO | 10113388 | 10/2010 |
| WO | 10122683 | 10/2010 |
| WO | 2010142813 | 12/2010 |
| WO | 11018408 | 2/2011 |
| WO | 2011032883 | 3/2011 |
| WO | 11068130 | 6/2011 |
| WO | 11068131 | 6/2011 |
| WO | 11114917 | 9/2011 |
| WO | 2011108575 | 9/2011 |
| WO | 11125475 | 10/2011 |
| WO | 2004110534 | 12/2014 |

* cited by examiner

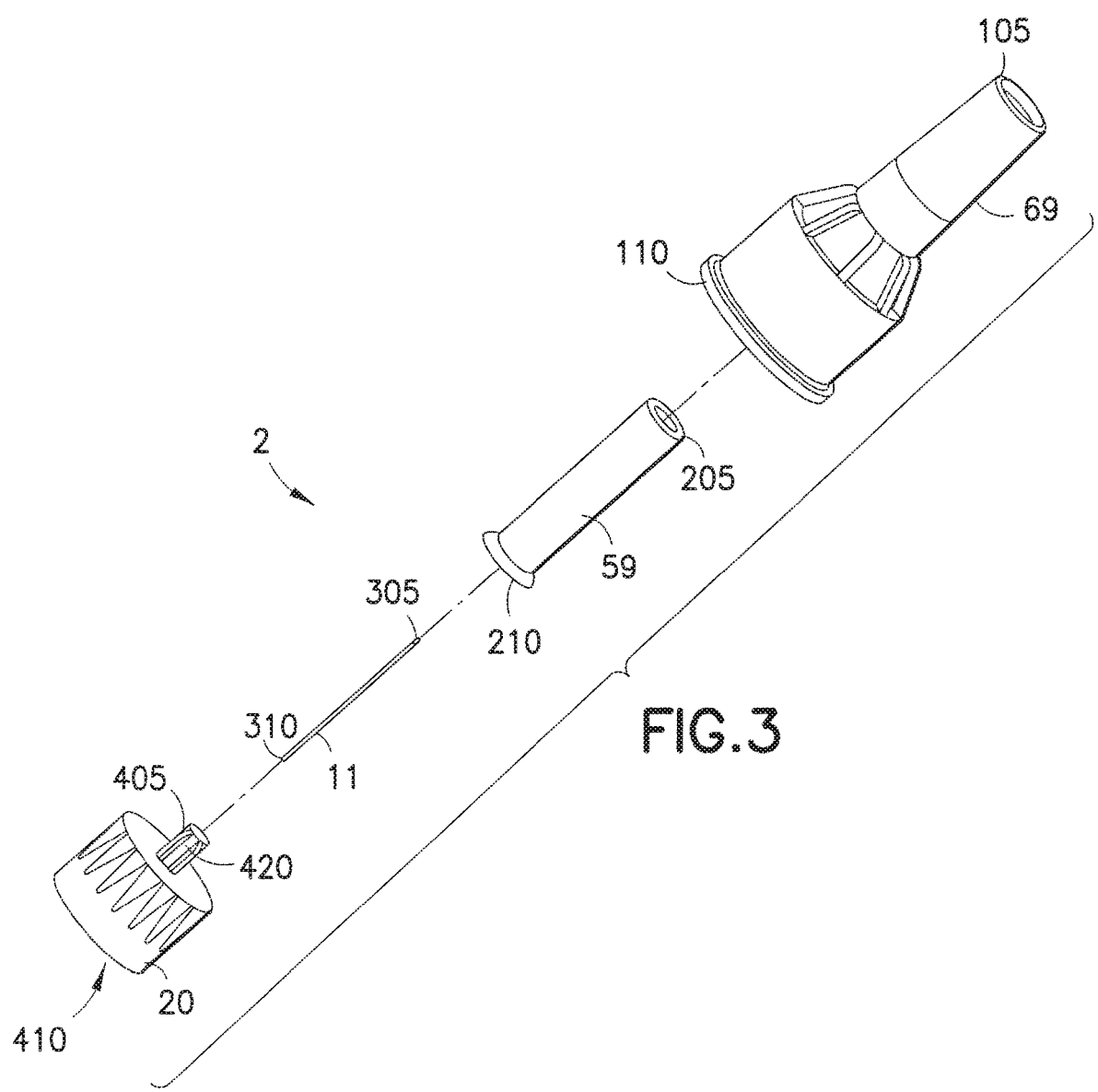

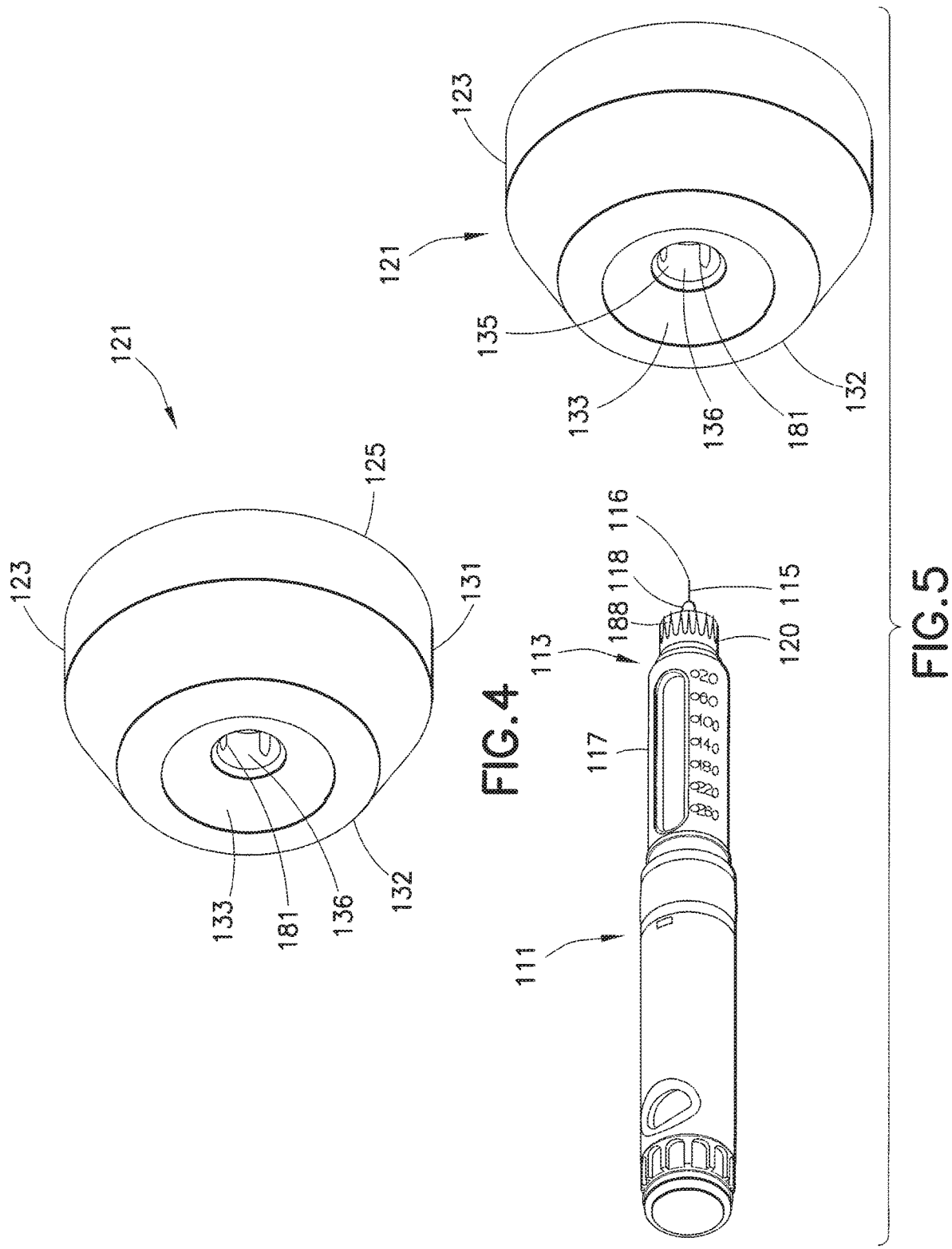

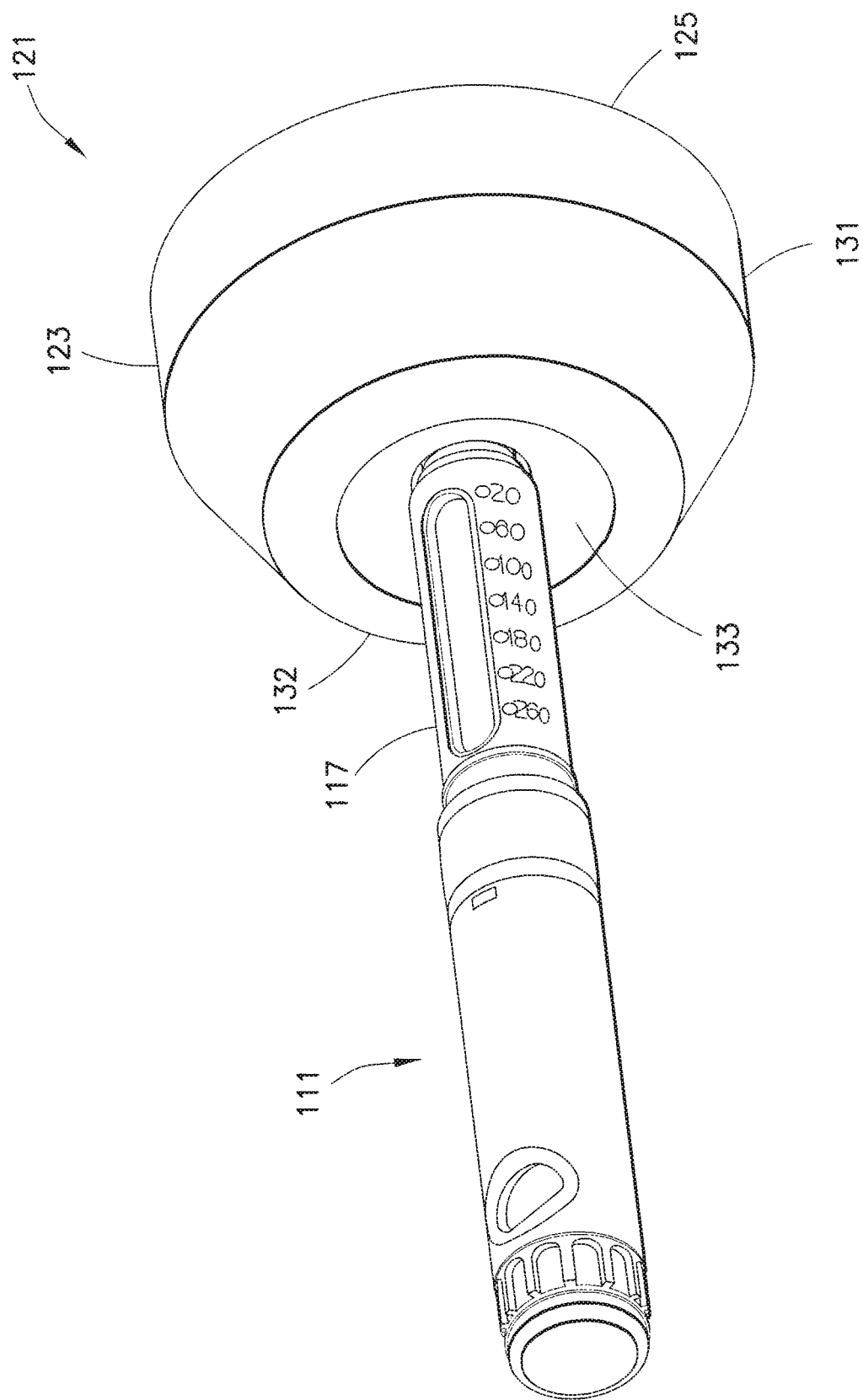

PEN NEEDLE REMOVAL DEVICE FOR A DRUG DELIVERY DEVICE

CROSS REFERENCE TO RELATED APPLICATION

This application is a continuation of U.S. patent application Ser. No. 15/863,655, filed Jan. 5, 2018 which is a continuation of U.S. patent application Ser. No. 14/517,395, filed Oct. 17, 2014, issued as U.S. Pat. No. 9,861,760 on Jan. 9, 2018, which is a continuation of U.S. patent application Ser. No. 13/513,159, filed May 31, 2012, issued as U.S. Pat. No. 8,882,706 on Nov. 11, 2014, which is a 371 of PCT/US2010/03086, filed Dec. 3, 2009, which claims the benefit under 35 U.S.C. § 119(e) from U.S. Provisional Patent Application Ser. No. 61/266,623, filed Dec. 4, 2009, the entire contents of which are hereby incorporated by reference.

FIELD OF THE INVENTION

The present invention relates generally to a device for removing a pen needle from a drug delivery device. More particularly, the present invention relates to a stand-alone device that removes a pen needle from a drug delivery device and ejects the removed pen needle for proper disposal thereof. Still more particularly, the present invention relates to a pen cap that removes a pen needle from a drug delivery device and ejects the removed pen needle for proper disposal thereof.

BACKGROUND OF THE INVENTION

Insulin and other injectable medications are commonly given with drug delivery devices, such as a drug delivery pen, whereby a disposable pen needle is attached to facilitate drug container access and allow fluid egress from the container through the needle into the patient.

Drug delivery devices, such as the exemplary drug delivery pen 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the drug delivery pen 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge 12. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

An exploded perspective view of a pen needle 2 of an exemplary drug delivery pen is shown in FIG. 3. The pen needle 2 includes the cover (outer shield) 69, an inner shield 59, a needle cannula 11, and a hub 20. A proximal end 310 of the needle cannula 11 is inserted into a center opening in the distal (patient) end 405 of the hub 20 until a predetermined length of the distal (patient) end 305 of the needle cannula 11 remains extended. The needle cannula 11 is secured by epoxy or adhesive in the distal end 405 of the hub 20 within the hub protrusion 420.

To protect users from injury and the needle cannula 11 from being damaged, the inner shield 59 covers the exposed portion of the needle cannula 11. The open proximal end 210 of the inner shield 59 is placed over the exposed portion of the needle cannula 11. The open proximal end 110 of the cover 69 envelops the inner shield 59, needle cannula 11, and hub 20.

The distal end 105 of the cover 69 is closed to prevent contamination and damage to the inner components of the pen needle 2, and to prevent injury to anyone who may handle it prior to use. The proximal end 410 of the hub 20 is typically covered by a sanitary paper or foil cover or label (not shown) glued on an end 110 of the cover 69. The pen needle is then ready for shipment to a user. When the user is ready to use the pen needle, the sanitary cover (not shown) is removed from the cover 69, the hub 20 is screwed onto a lower housing 17 of a standard pen 100 (FIGS. 1 and 2), and the cover 69 and shield 59 are separately removed from the hub 20/cannula 11 subassembly by a pulling action. The distal end 205 of the inner shield 59 is closed to cover the distal end 305 of the needle cannula 11 after the cover 69 is removed to protect the user from an accidental needle stick. The inner shield 59 is then removed to access the needle cannula 11.

Following an injection with a drug delivery pen 100, as shown in FIGS. 1 and 2, the used pen needle, which includes the hub 20 and needle 11, or "sharps", are unthreaded from the lower housing 17 and properly disposed of, such as in a sharps container. Used sharps may become contaminated by body fluids and the like creating a hazard for anyone that may handle them following their use. Sharps disposal containers store the disposed sharps and prevent unintentional contact with any object disposed therein.

As noted above, removing a used pen needle from the drug delivery pen 100 for proper disposal presents a safety risk because the used needle 11 is exposed. Accordingly, a need exists for removing a used pen needle from a drug delivery pen that substantially reduces or eliminates accidental needle sticks.

Existing drug delivery pens are disclosed in U.S. Pat. No. 7,645,264 to Marsh et al., which issued on Jan. 12, 2010, and U.S. Patent Application Publication No. 2007/0149924 to R.

Marsh, which was published on Jun. 28, 2007, the entire contents of both of which are hereby incorporated by reference.

SUMMARY OF THE INVENTION

In accordance with an aspect of the present invention, a removal device removes a used pen needle from a drug delivery device without exposing the needle.

In accordance with another aspect of the present invention, a stand-alone removal device removes a used pen needle from a drug delivery device without exposing the needle.

In accordance with another aspect of the present invention, a removal device is disposed in a cap of a drug delivery device for removing a used pen needle from a drug delivery device without exposing the needle.

The foregoing objects are basically attained by providing a removal device for removing and disposing of a pen needle connectable to a drug delivery device. The removal device includes a body having a cavity for receiving the pen needle of the drug delivery device. A patient end of a needle of the pen needle is covered by the body of the removal device. An ejector is movably connected to the body for engaging the received pen needle and selectively ejecting the engaged pen needle from the body. The ejected pen needle can be properly disposed of in a sharps container without exposing a needle of the pen needle, thereby substantially preventing an accidental needle stick.

The foregoing objects are also attained by providing a method of removing a pen needle from a drug delivery device without exposing a needle thereof. The pen needle of the drug delivery device is inserted in a cavity of a body of a removal device. A patient end of a needle of the pen needle is covered by the body of the removal device. The received pen needle is engaged with an ejector movably connected to the body. The drug delivery pen is removed from the body of the removal device such that the engaged pen needle is retained by the body. The engaged pen needle is selectively ejected from the body with the ejector. The ejected pen needle can be properly disposed of in a sharps container without exposing a needle of the pen needle, thereby substantially preventing an accidental needle stick.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which:

FIG. 3 is an exploded perspective view of a pen needle of the drug delivery pen of FIG. 1;

FIG. 4 is a perspective view of a pen needle removal device according to a first exemplary embodiment of the present invention;

FIG. 5 is a perspective view of the pen needle removal device of FIG. 4 about to receive a pen needle of a drug delivery device;

FIG. 6 is a perspective view of the pen needle removal device of FIG. 4 receiving the pen needle of the drug delivery device;

Throughout the drawings, like reference numbers will be understood to refer to like parts, components and structures.

DETAILED DESCRIPTION OF THE EXEMPLARY EMBODIMENTS

Figure 1:
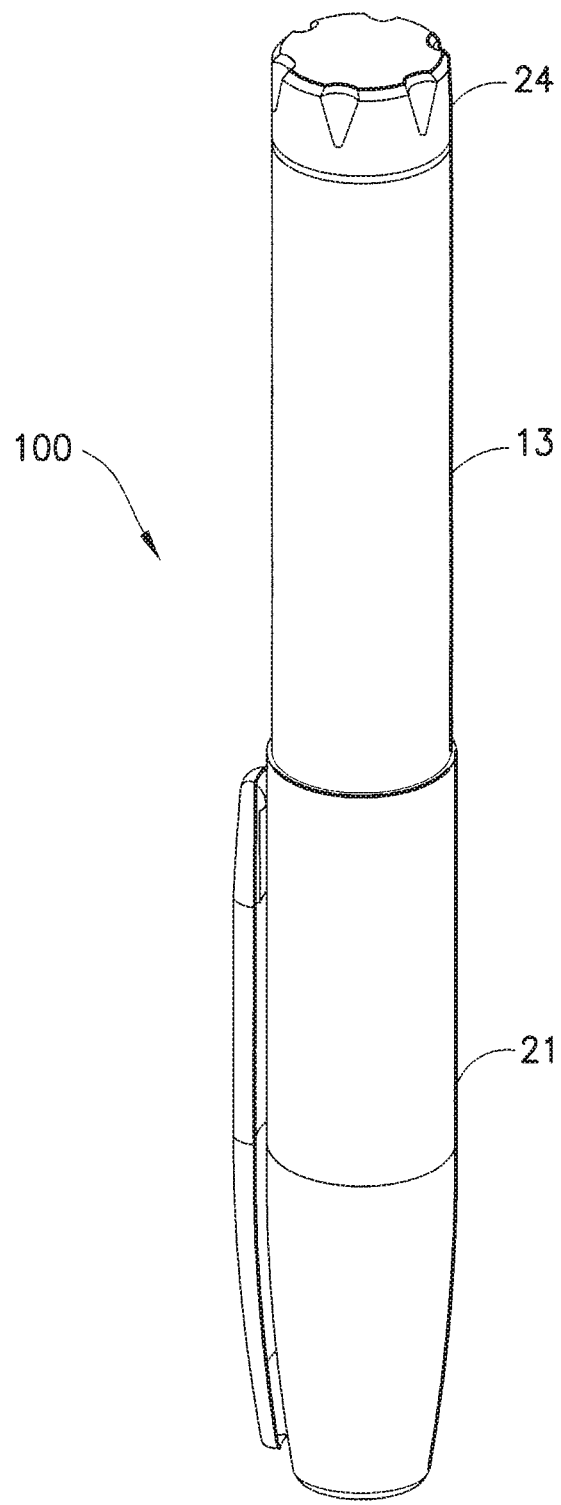
FIG. 1 is a perspective view of an assembled drug delivery pen.
Figure 2:
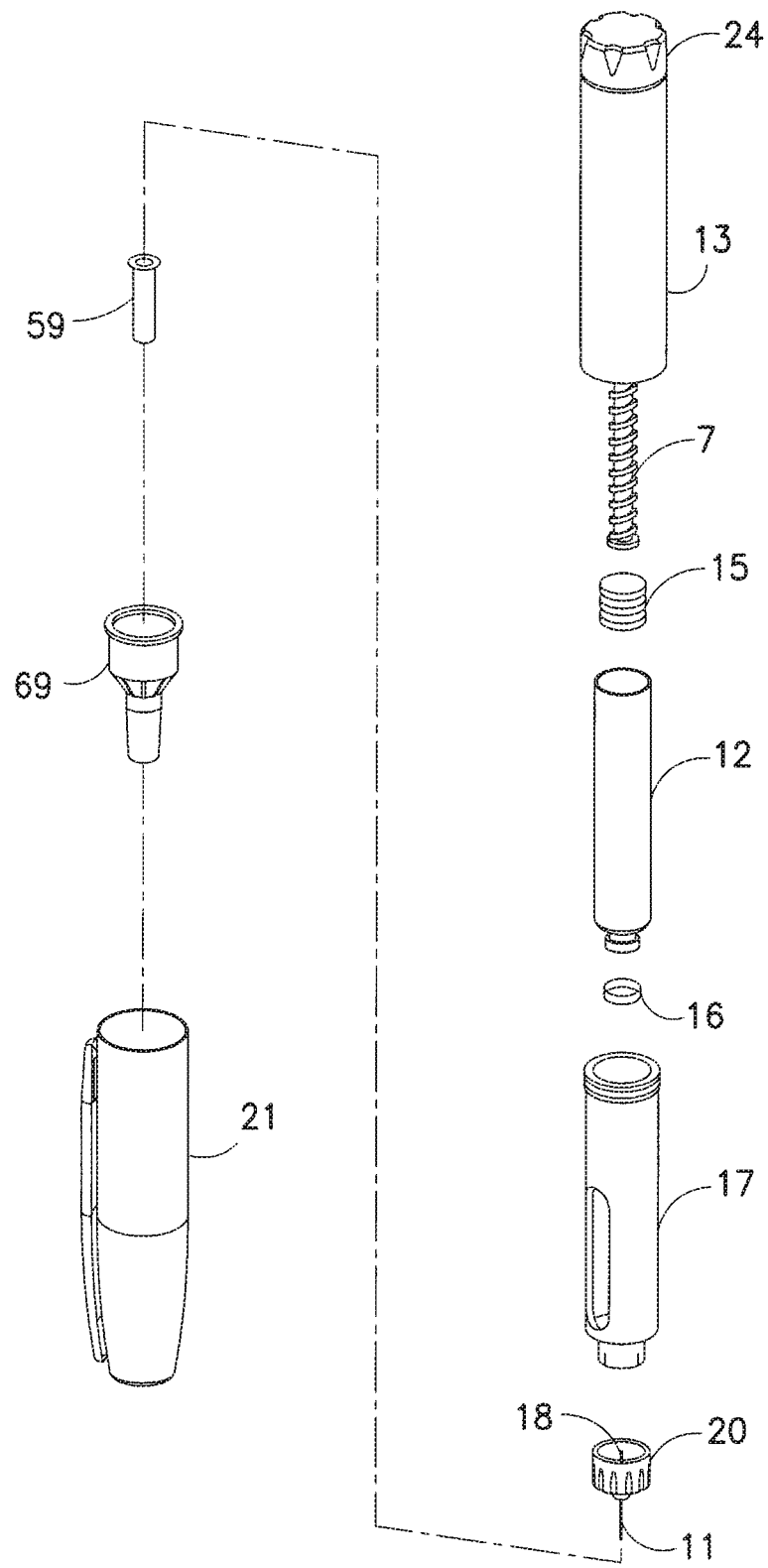
FIG. 2 is an exploded perspective view of the components of the drug delivery pen of FIG. 1.

With reference to FIGS. 4-9, a removal device 121 for removing and disposing of a pen needle 113 connectable to a drug delivery device 111, in accordance with a first exemplary embodiment of the present invention, includes a body 123 having a cavity 141 for receiving the pen needle of the drug delivery device such that a patient end 116 of a needle 115 of the pen needle is covered by the body. An ejector 151 is movably connected to the body 123 for engaging the received pen needle 113 and selectively ejecting the engaged pen needle from the body. The ejected pen needle 113 can be properly disposed of in a sharps container without exposing a needle 115 of the pen needle, thereby substantially preventing an accidental needle stick. While the following description and details of exemplary embodiments of the present invention are generally disclosed with respect to a typical drug delivery device, such as the drug delivery pen shown in FIGS. 1 and 2, the present invention can more broadly apply to a pen needle for use in conjunction with, or incorporated onto, other injection devices, such as syringes and infusion devices. The assembly and operation of a typical drug delivery pen 100, as shown in FIGS. 1 and 2, is described in U.S. Pat. No. 7,465,264, issued on Jan. 12, 2010, which is hereby incorporated by reference in its entirety.

As described above, the drug delivery pen 111 includes a lower housing 117 to which a hub 120 of the pen needle 113 is threadably connected, as shown in FIG. 5. The pen needle 113 includes a needle 115 and a hub 120. A proximal end of the needle 115 is inserted into a center opening in the distal (patient) end of the hub 120 until a predetermined length of the distal (patient) end 116 of the needle 115 remains extended. The needle 115 is secured by epoxy or adhesive in the distal end of the hub 120 within the hub protrusion 118. A plurality of recesses 188 are formed in the outer surface of the hub 120, as shown in FIG. 5.

Figure 7:
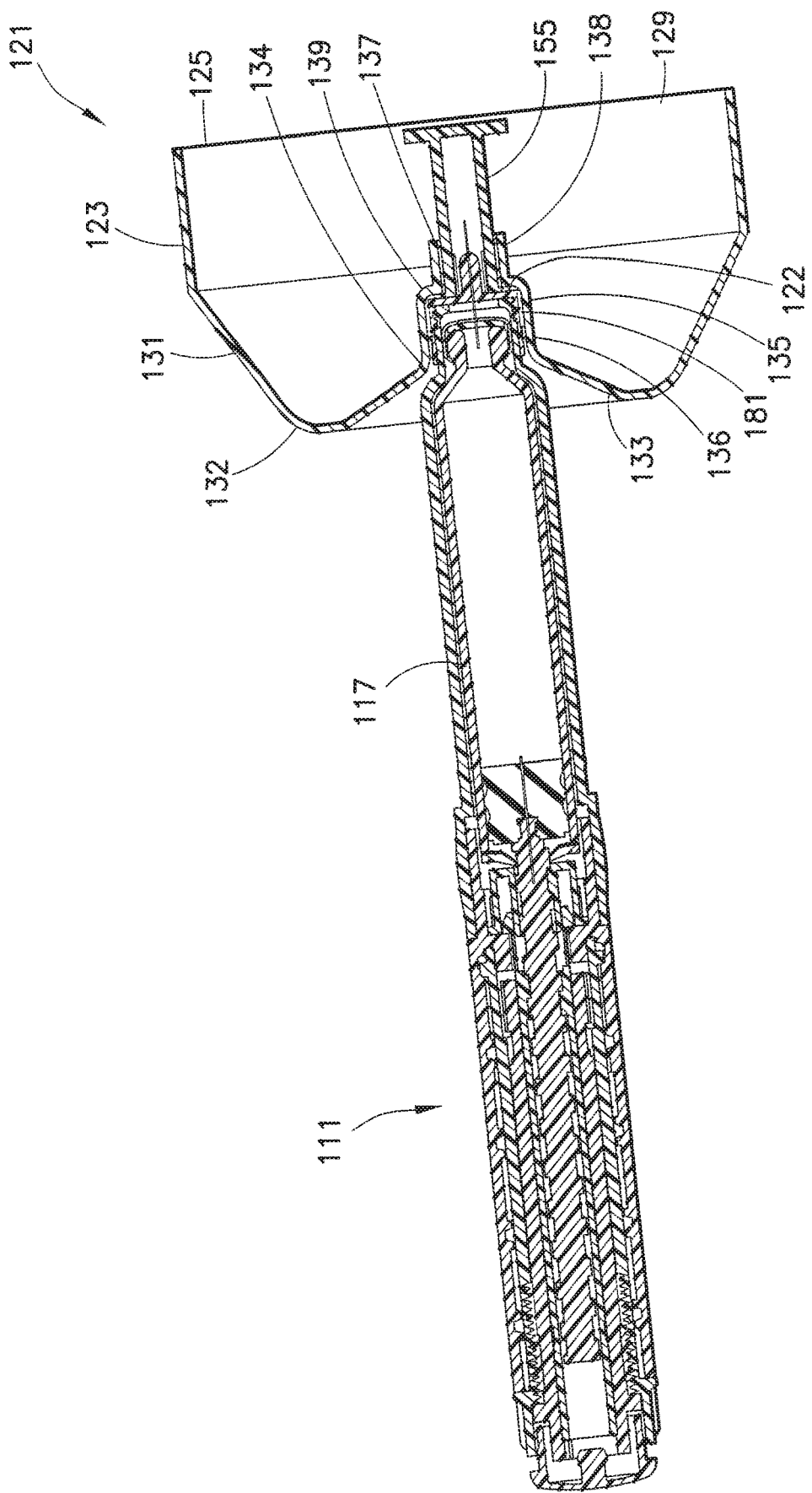
FIG. 7 is an elevational view in cross-section of the pen needle removal device of FIG. 4 receiving the pen needle of the drug delivery device.

The pen needle removal device 121 includes a body 123, as shown in FIG. 4. The body 123 includes an outer wall 131, an inwardly tapering wall 133, and an inner wall 135, as shown in FIG. 7. The outer wall 131 extends upwardly from a free end 125 to an upper edge 132. The free end 125 of the outer wall 131 forms a base, thereby allowing the removal device 121 to sit flat on a surface to facilitate removing a pen needle 113 from the drug delivery device 111. The inwardly tapering wall 133 tapers inwardly from the upper edge 132 to an inner edge 134. The inner wall 135 extends toward the base from the inner edge 134. The inner wall 135 preferably has a first portion 136 having a first diameter and a second portion having a second diameter. The first portion 136 of the inner wall 135 extends from the inner edge 134. Inwardly extending ribs 181 can be formed on an inner surface of the first portion 136 of the inner wall, as shown in FIGS. 4 and 5. An inwardly extending shoulder 139 is formed at the end of the first portion 136, and the second portion 138 extends toward the base from the shoulder 139. The first diameter is larger than the second diameter. A first opening 137 is formed in an end of the inner wall 135 to receive the ejector 151. Preferably, the body 123 of the removal device 121 is unitarily formed as a single piece. Although the removal device 121 is shown having an inwardly tapering wall to form a concave configuration, the removal device may be configured to be convex or planar. Preferably, the removal device 121 is made of plastic.

A cavity 141 is formed in the body 123 and is defined by the inwardly tapering wall 133 and the inner wall 135. The cavity 141 accommodates a pen needle 113, as shown in FIG. 7. The first portion 136 of the inner wall 135 accommodates the hub 120 of the pen needle, as shown in FIGS. 6 and 7. Preferably, an interference fit is formed between the first portion 136 of the inner wall 135 and the pen needle hub 120. The shoulder 139 is a stop to limit insertion of the drug delivery device 1 by engaging a surface of the pen needle hub 120. The hub protrusion 118 is received within the second portion 138 of the inner wall 135.

The ejector 151 has a flange 153 and a wall 155 extending therefrom. Feet 157 extend outwardly from the free end of the wall 155. The ejector 151 extends through the opening 137, as shown in FIGS. 5-9. The feet 157 prevent the ejector from being withdrawn past the shoulder 139 and the flange 153 prevents the ejector from being pushed through the first opening 137. A second opening 129 is formed in the free end 125 of the outer wall 131 to provide access to the ejector 151. The flange 153 facilitates selective manipulation of the ejector by the user.

Figure 8:
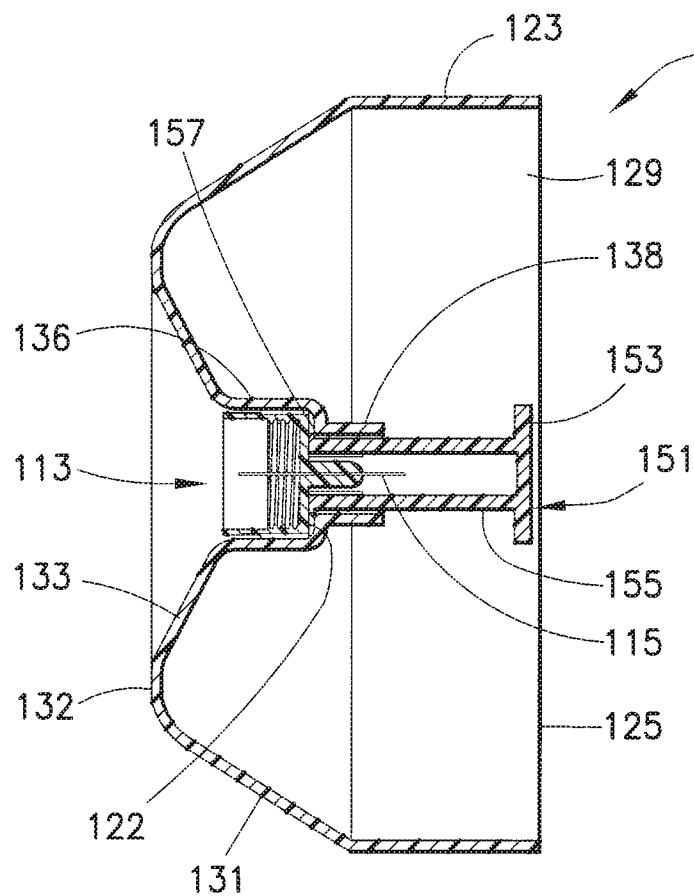
FIG. 8 is an elevational view in cross-section of the pen needle removal device of FIG. 4 retaining the pen needle after removing the drug delivery device.

To remove the pen needle 113 from the drug delivery device 111, such as after the pen needle has been used to make an injection, the drug delivery device is inserted in the cavity 141 of the removal device 121 until the base surface 122 of the pen needle hub 120 abuts the shoulder 139 of the removal device, as shown in FIG. 7. The base of the removal device 121 can be placed on a table to facilitate insertion of the drug delivery device 111, thereby further preventing accidental needle sticks by not requiring the user to hold the removal device. The hub protrusion 118 and needle 115 are disposed within the wall 155 of the ejector 151. An interference fit is created between the pen needle hub 120 and the second portion 136 of the inner wall 135 of the removal device 121, thereby securely retaining the pen needle 113 within the removal device while the lower housing 117 of the drug delivery device 111 is rotated and unthreaded from the pen needle 113, as shown in FIG. 8. The friction between the hub 120 of the pen needle 113 and the second portion 136 of the inner wall 135 of the removal device 121 prevents movement of the pen needle as the drug delivery device 111 is unthreaded from the removal device 121. Preferably, the diameter of the second portion 136 is less than that of the pen needle hub 120 to create the interference fit therebetween. The pen needle 113 is securely retained within the removal device 121 with the patient end 116 of the needle 115 shielded within the wall 155 of the ejector 151 such that the user can carry the removal device 121 with the pen needle 113 disposed therein until the pen needle can be properly disposed of, such as in a sharps container.

Alternatively, the ribs 181 formed on the second portion 136 of the inner wall 135 of the removal device 121 engage the recesses 188 formed in the pen needle hub 120. Accordingly, the ribs 181 prevent rotation of the pen needle hub 120 such that the drug delivery device 111 can be unthreaded from the removal device 121 while securely retaining the pen needle 113 in the removal device.

Figure 9:
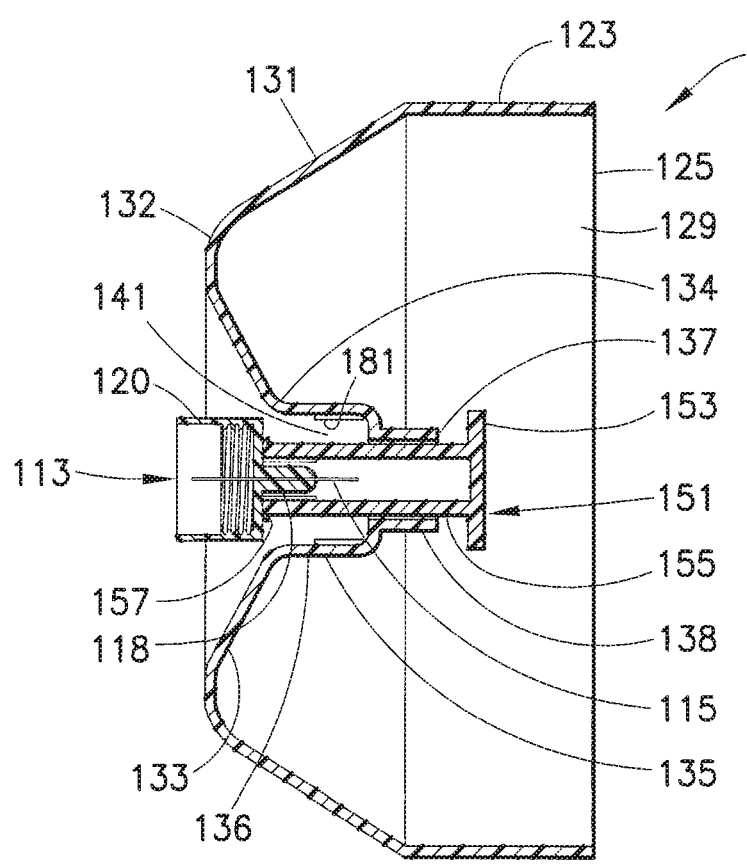
FIG. 9 is an elevational view in cross-section of the pen needle removal device of FIG. 4 ejecting the pen needle.

When the pen needle 113 is to be ejected from the removal device 121, the user pushes the ejector flange 153 inwardly in a direction substantially opposite to the insertion direction of the drug delivery device, as shown in FIG. 9. The ejector 151 is moved in a direction substantially parallel to a longitudinal axis of the needle 115. The second portion 138 of the inner wall 135 guides movement of the ejector wall 155 during ejection of the pen needle 113. The feet 157 engage the base surface 122 of the hub 120, thereby overcoming the interference fit between the hub 120 and the second portion 136 of the inner wall 135 such that the pen needle 113 can be properly disposed of.

Figure 11:
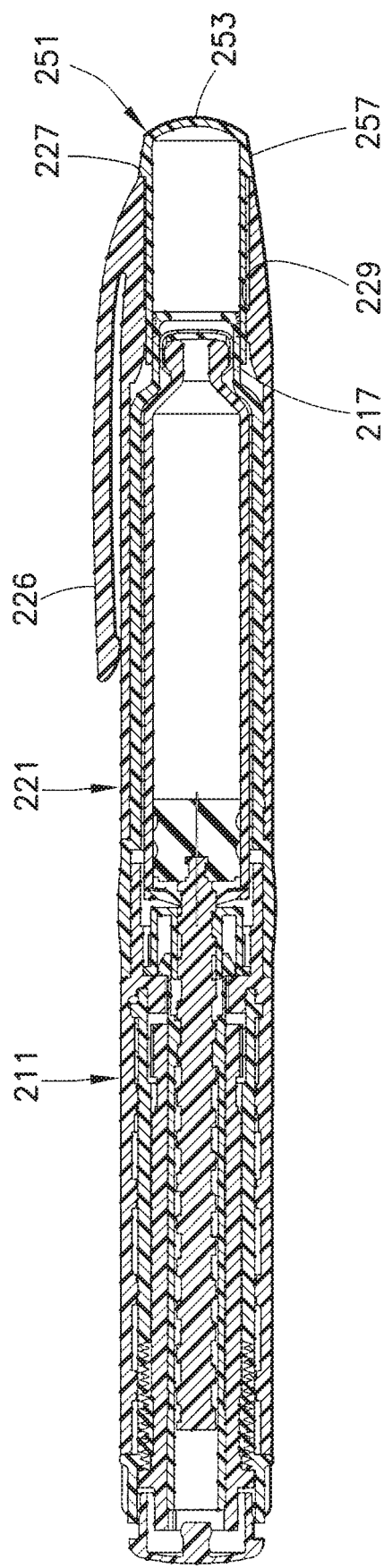
FIG. 11 is an elevational view in cross-section of the pen needle removal device of FIG. 10.
Figure 12:
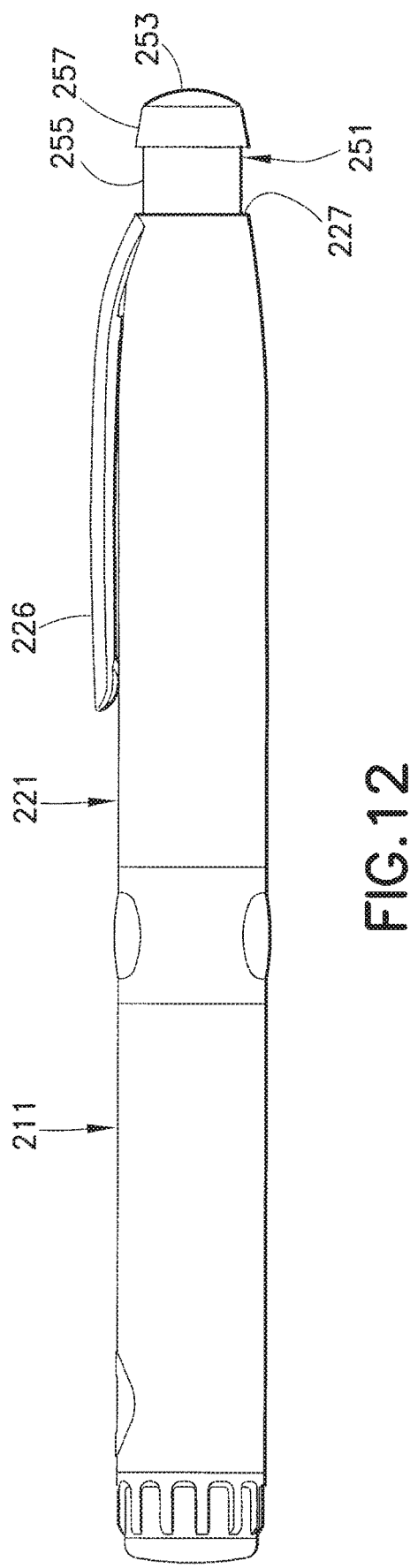
FIG. 12 is an elevational view of the pen needle removal device of FIG. 10 in which a pen needle is connected to the drug delivery device.
Figure 13:
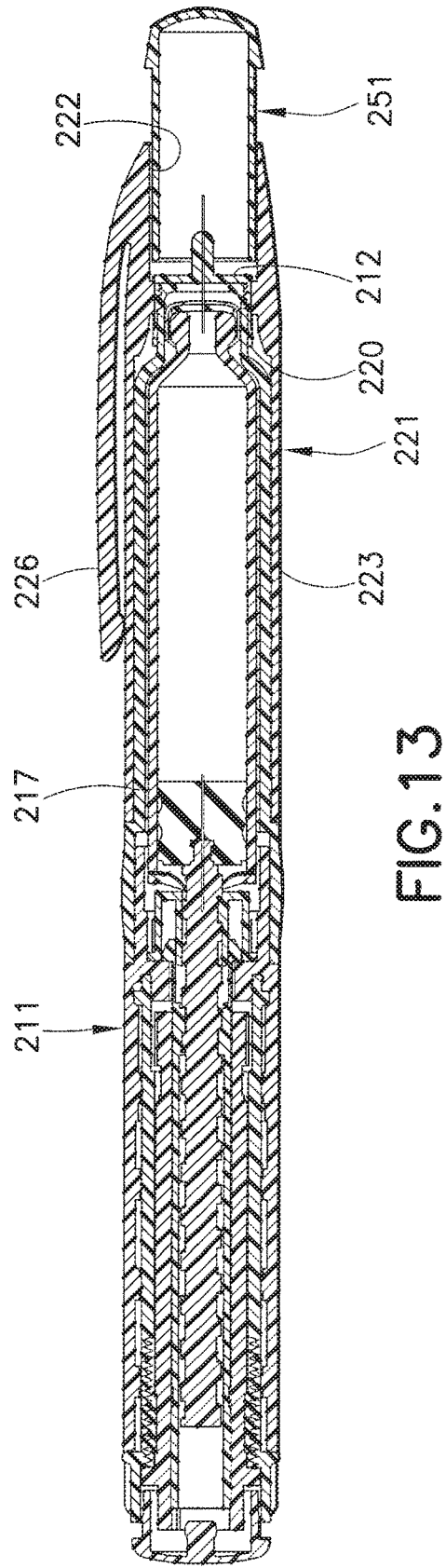
FIG. 13 is an elevational view in cross-section of the pen needle removal device of FIG. 12.

In a second exemplary embodiment of the present invention shown in FIGS. 10-17, the removal device comprises a cap 221. As described above, the drug delivery pen 211 includes a lower housing 217 to which a hub 220 of the pen needle 213 is threadably connected, as shown in FIG. 13. The pen needle 213 includes a needle 215 and a hub 220. A proximal end of the needle 215 is inserted into a center opening in the distal (patient) end of the hub 220 until a predetermined length of the distal (patient) end 216 of the needle 215 remains extended. The needle 215 is secured by epoxy or adhesive in the distal end of the hub 220 within the hub protrusion 218.

The pen needle removal device, or cap, 221, as shown in FIGS. 10-17, includes a body 223 having first and second openings 222 and 224 disposed at opposite ends thereof. The drug delivery device 211 is inserted through the second opening and the ejector 251 is inserted through the first opening 222. A flexible clip 226 is connected to the body 223 of the cap 221 to facilitate carrying the drug delivery device 211 by the user. An inwardly extending retaining ring 229 is disposed on an inner surface 228 of the body 223, as shown in FIGS. 11 and 13-15. The retaining ring 229 preferably extends around an entire inner circumference of the cap body 223. A cavity 241 within the cap 221 is defined by the body 223 of the cap.

Figure 10:
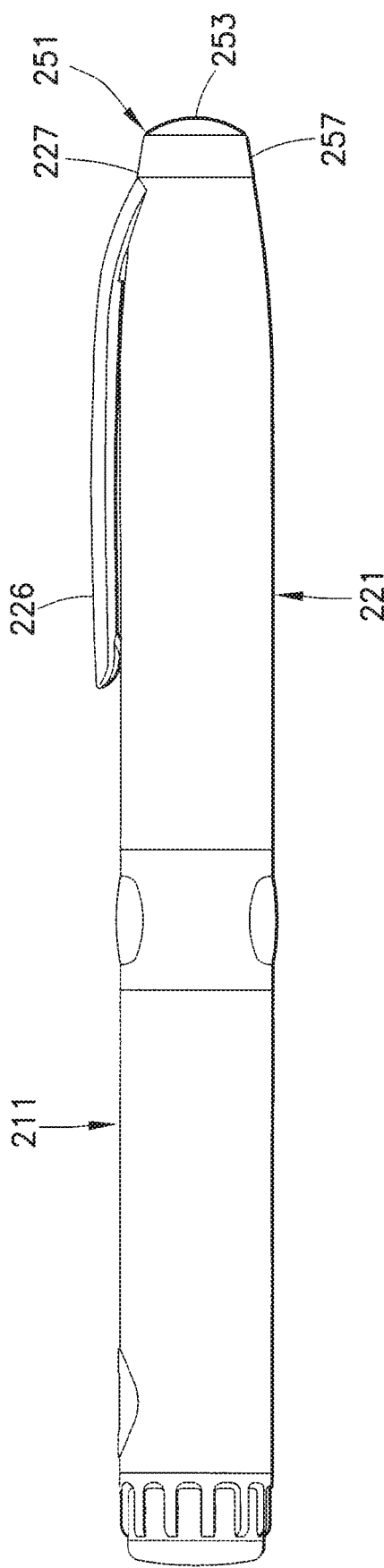
FIG. 10 is an elevational view of a pen needle removal device according to a second exemplary embodiment of the present invention.

The ejector 251 has a base 253 from which a wall 255 extends outwardly, as shown in FIGS. 11-15. A tab 257 extends outwardly from the wall 255 proximate the base 253. The tab 257, which preferably extends around the entire circumference of the wall 255, engages an end 227 of the cap 221, as shown in FIGS. 10 and 11, to limit movement of the ejector 251 into the cap 221.

Figure 16:
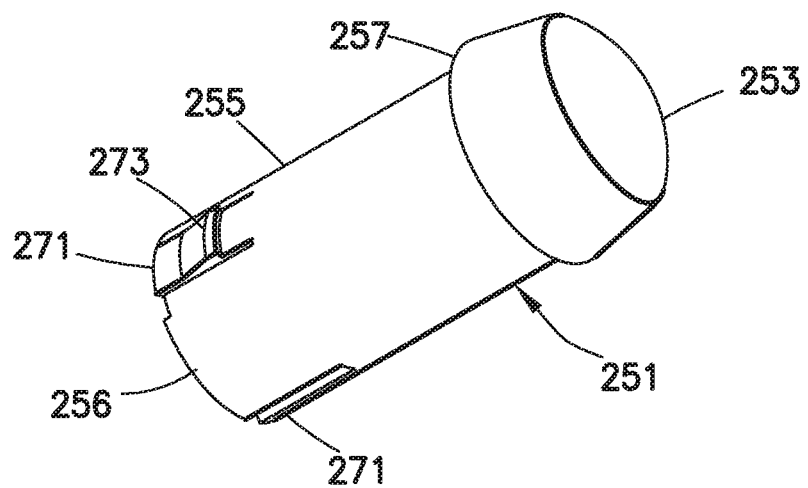
FIG. 16 is a perspective view of the ejector of FIG. 10.
Figure 17:
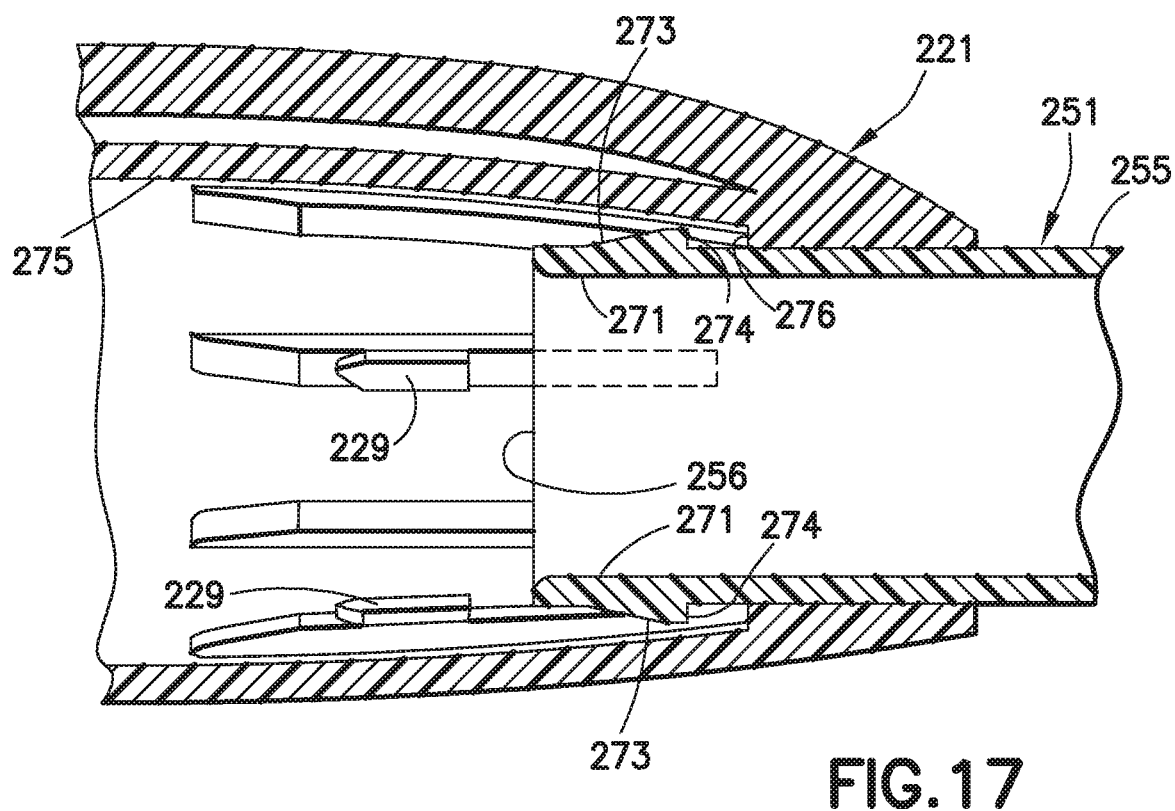
FIG. 17 is an enlarged elevational view of the ejector and cap of FIG. 11.

The ejector 251 can have a plurality of flexible fingers 271 disposed proximate an end 256 of the ejector wall 255, as shown in FIGS. 16 and 17. A tab 273 extends outwardly from each of the flexible fingers 271. Each tab 273 has a flat surface 274 that abuts an end 276 of a recess 275 formed in an inner surface 228 of the cap 221. The flexible fingers 271 flex inwardly to allow insertion of the ejector 251 into the cap 221. The engagement of the flat surface 274 of the flexible finger tab 271 with the end 276 of the recess 275 in the cap body 223 prevents complete withdrawal of the ejector 251 from the cap 221.

Figure 15:
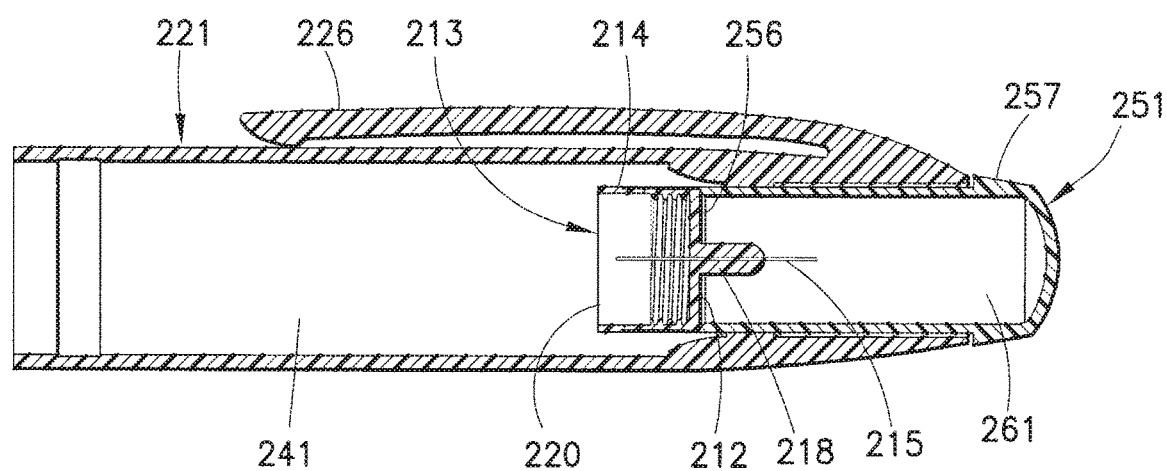
FIG. 15 is an elevational view in cross section of the pen needle removal device ejecting a pen needle.

The ejector 251 is movable between first and second positions. In a first position, as shown in FIGS. 10, 11 and 15, the ejector 251 is pushed into the cap body 223 such that the ejector tab 257 abuts the end 227 of the cap 221. As shown in FIG. 11, the cap wall 255 is received between the retaining ring 229 and the threaded portion of the lower housing 217. The end 256 of the ejector 251 also abuts the retaining ring 229. When the ejector is in the first position, it is an indication to the user that a pen needle is not connected to the drug delivery device 211.

Figure 14:
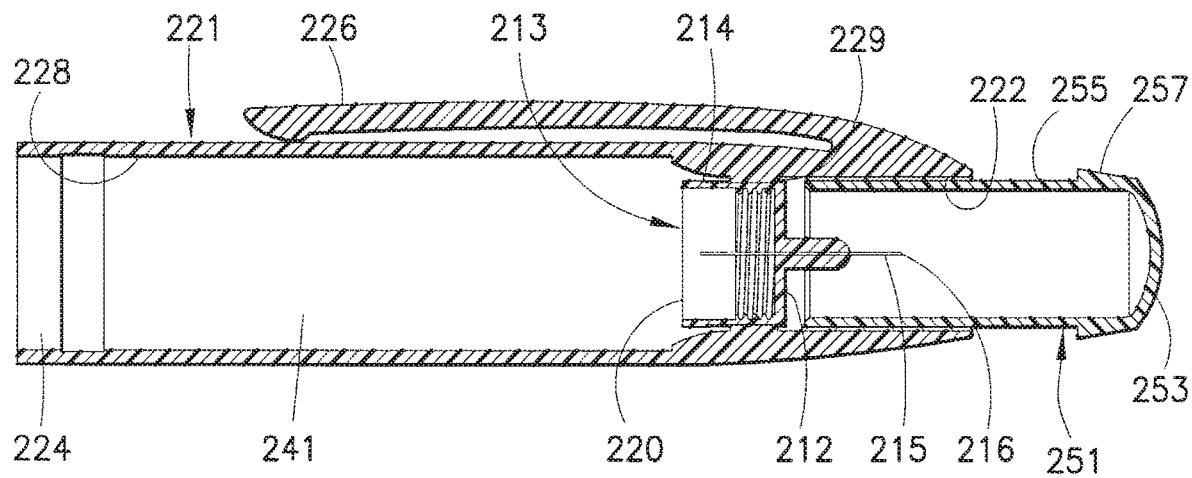
FIG. 14 is an enlarged elevational view in cross-section of the pen needle removal device of FIG. 13 after removing a pen needle from the drug delivery device.

In the second position, the ejector 251 is partially withdrawn from the cap body 223, as shown in FIGS. 12-14. The ejector 251 being in the second position is an indication to the user that a pen needle 213 is connected to the drug delivery device 211. The insertion of the pen needle 213 causes the base 212 of the hub 220 to partially push the ejector 251 out of the cap 221. Movement of the ejector 221 out of the cap 251 is limited by engagement of the flat surface 274 of the flexible finger tab 273 with the end 276 of the recess 275 in the cap body 223.

When a drug delivery device 211 with a pen needle 213 attached thereto is inserted in the cavity 241 of the cap 221, a base surface 212 of the hub 220 engages the end 256 of the ejector wall 255 and moves the ejector from the first position (FIG. 11) to the second position (FIG. 12). The drug delivery device 211 is further inserted in the cap 221 until an interference fit is created between the outer surface of the hub wall 214 and the retaining ring 229, as shown in FIGS. 13 and 14, thereby preventing further insertion of the drug delivery device. The drug delivery device 211 can then be rotated and unthreaded from the pen needle 213 such that the pen needle is securely retained in the cap 221, as shown in FIG. 14. Friction between the retaining ring 229 and the pen needle hub 220 prevents the pen needle from rotating and being removed with the drug delivery device 211. The patient end 216 of the needle 215 is covered by the ejector 251, thereby preventing accidental needle sticks. The user can carry the cap 221 with the pen needle 213 securely retained therein until the pen needle can be properly disposed of such as in a sharps container.

Alternatively, the retaining ring 229 can be formed as a plurality of ribs around the inner surface of the cap 221 that engage the recesses 188 (FIG. 5) in the pen needle hub 220. When the drug delivery device 211 is rotated, the retaining ring ribs 229 engage the recesses in the pen needle hub 220, thereby preventing the pen needle 213 from rotating with the drug delivery device. Accordingly, the pen needle 213 is securely retained in the cap 221.

When the pen needle 213 is to be ejected from the cap 221, the user pushes the base 253 of the ejector 251 inwardly in a direction substantially opposite to the insertion direction of the drug delivery device 211, as shown in FIG. 15. The ejector 251 is moved in a direction substantially parallel to a longitudinal axis of the needle 215. The end 256 of the ejector wall 255 engages the base surface 212 of the hub 120, thereby overcoming the interference fit between the hub 220 and the retaining ring 229 of the cap 221 such that the pen needle 213 can be properly disposed of. The ejector tab 257 abuts the end 227 of the cap 221, thereby limiting insertion of the ejector 251 into the cap.

The ejector cavity 261, which is defined by the base 253 and the wall 255, can accommodate an inner shield 59 (FIG. 2) disposed on the hub protrusion 218. To perform an injection, the user removes the cap 221 from the drug delivery device 211, thereby providing access to the pen needle 215. Pulling the cap overcomes the interference fit between the pen needle hub 220 and the retaining ring 229, such that the pen needle hub remains connected to the drug delivery device 211. Alternatively, the retaining ring ribs 229 do not engage the walls of the pen needle hub 220 so that the drug delivery device can be pulled outwardly from the cap 221 with the pen needle 213 connected to the drug delivery device. The inner shield 59 is then removed from the pen needle hub 220 so that the injection can be made. The used pen needle is then reinserted into the cap 221, as described above, such that the ejector 251 moves to the second position, as shown in FIG. 12, thereby indicating the presence of a pen needle. The used pen needle can then be properly disposed of as described above.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A system comprising:
  a drug delivery device configured to connect with a hub of a pen needle; and
  and a cap comprising
  a body removably connectable to the drug delivery device, said body having a cavity for receiving the pen needle connected to the drug delivery device such that at least a portion of the hub of the pen needle directly contacts at least a portion of an inner wall of the cavity and is retained within the cavity of the body; and
  an axially movable ejector connected to the body such that a patient end of the pen needle received in said cavity is covered by the ejector,
  wherein
  selectively moving the ejector with respect to the body causes ejecting the pen needle out of said body, and
  said ejector is in a withdrawn position when said body is connected to the drug delivery device to which the pen needle is connected.

2. The system according to claim 1, wherein
  said cavity has a diameter smaller than a diameter of the hub of the pen needle to create an interference fit with the received pen needle; and
  an end of said ejector engages the hub of the pen needle such that movement of said ejector moves the pen needle out of said cavity.

3. The system according to claim 1, wherein
  at least a portion of the received pen needle is disposed within said ejector.

4. The system according to claim 1, wherein
  said body is formed separately from the drug delivery device and comprises a cover for at least a portion of the drug delivery device.

5. The system according to claim 1, wherein
  said body has a base to allow said body to sit on a planar surface.

6. The system according to claim 1, wherein the pen needle is retained within said body when the drug delivery device is unthreaded from said hub of said pen needle.

7. The system according to claim 1, wherein a substantial portion of said ejector is pushed into said body to eject the pen needle therefrom.

8. The system according to claim 1, wherein said ejector is in an inserted position when said body is connected to the drug delivery device to which the pen needle is not connected.

9. The system according to claim 1, wherein a tab extends outwardly from said ejector limiting movement of said ejector into said body.

10. The system according to claim 1, wherein
said body is removable from the drug delivery device with the pen needle retained within said cavity; and
said ejector is pushed into said body to eject the pen needle therefrom.

11. The system according to claim 1, wherein
said ejector contacts a distal face of said hub of the pen needle.

12. The system according to claim 1, wherein the drug delivery device comprises:
a lower housing including a medicament storage volume and an outlet to connect with the hub of the pen needle; and
an upper housing including a mechanism to move a dose of the medicament out of the storage volume via the pen needle for injection of the dose of the medicament.

13. The system of claim 12, wherein the mechanism comprises at least one of a dose setting component, a dose correcting component, and a dose injection component.

14. A method comprising the steps of:
connecting a hub of a pen needle to a drug delivery device;
performing an injection with the drug delivery device via the pen needle; and
inserting the pen needle of the drug delivery device into a cavity of a body of a cap removably connectable to the drug delivery device such that at least a portion of the hub of the pen needle directly contacts at least a portion of an inner wall of the cavity and at least one inwardly extending rib within the cavity, the inwardly extending rib engages at least one recess in at least a portion of the hub of the pen needle;
engaging the inserted pen needle with an ejector movably connected to the body such that a patient end of the inserted pen needle is covered by the ejector;
rotating the body with respect to the drug delivery device;
removing the drug delivery device from the body such that the inserted pen needle is retained by the body; and
moving the ejector with respect to the body to eject the engaged pen needle from the body,
wherein said ejector is in a withdrawn position when said cap is connected to the drug delivery device to which the pen needle is connected.

15. The method according to claim 14, wherein
said cavity has a diameter smaller than a diameter of the hub of the pen needle to create an interference fit with the inserted pen needle; and
an end of said ejector engages the hub of the pen needle such that said moving of the ejector moves the pen needle out of said cavity.

16. The method according to claim 14, wherein
at least a portion of the inserted pen needle is disposed within said ejector.

17. The method according to claim 14, wherein a substantial portion of said ejector is pushed into said body to eject the pen needle therefrom.

18. The method of claim 14, further comprising setting a dose of the injection.

19. The method of claim 18, further comprising correcting a set dose of the injection.

\* \* \* \* \*